(12) United States Patent
Choi

(10) Patent No.: US 6,684,418 B2
(45) Date of Patent: Feb. 3, 2004

(54) INFANT'S CHAMBER POT HAVING HEALTH CHECKING FUNCTION

(76) Inventor: Keun Seob Choi, 6-4 Gongse-ri, Kilheung-eup, Yongin-si, Kyungki-do, 449-900 (KR)

( * ) Notice: Subject to any disclaimer, the term of this patent is extended or adjusted under 35 U.S.C. 154(b) by 0 days.

(21) Appl. No.: 10/296,560
(22) PCT Filed: May 22, 2001
(86) PCT No.: PCT/KR01/00848
§ 371 (c)(1), (2), (4) Date: Nov. 25, 2002
(87) PCT Pub. No.: WO01/89355
PCT Pub. Date: Nov. 29, 2001

(65) Prior Publication Data
US 2003/0131408 A1 Jul. 17, 2003

(51) Int. Cl.$^7$ ................................................ A47K 11/04
(52) U.S. Cl. .................... 4/483; 4/314; 4/902; 600/300
(58) Field of Search ............................ 4/314, 661, 902, 4/483; 600/300

(56) References Cited

U.S. PATENT DOCUMENTS 3,680,151 A    8/1972  Boardman et al.
5,893,178 A  * 4/1999  Wosiek ........................... 4/483
6,524,239 B1 * 2/2003  Reed et al. ................. 600/300
6,572,564 B2 * 6/2003  Ito et al. ..................... 600/573

FOREIGN PATENT DOCUMENTS

EP          0 336 434         4/1989

* cited by examiner

Primary Examiner—Charles E. Phillips
(74) Attorney, Agent, or Firm—Darby & Darby

(57) ABSTRACT

Disclosed are an infant's chamber pot having a health checking function and an operating method thereof. The infant's chamber pot comprises a power source section; a temperature sensor installed on a bottom surface inside the chamber pot to measure a temperature of stool; a controller electrically connected to the temperature sensor, operated by a voltage supplied from the power source section and having a memory part in which melody signal data and warning signal data are stored, the controller selectively outputting the melody signal data or the warning signal data depending upon the stool temperature sensed by the temperature sensor, by comparing the stool temperature with a normal threshold temperature; and a speaker electrically connected to an output terminal of the controller, the speaker converting the signal data outputted from the controller into an audible signal and then, outputting the audible signal.

9 Claims, 3 Drawing Sheets

_US 6,684,418 B2_

INFANT'S CHAMBER POT HAVING HEALTH CHECKING FUNCTION

TECHNICAL FIELD

The present invention relates to an infant's chamber pot having a health checking function, in which a temperature sensor is disposed in a manner such that a character signal or a sound signal for notifying the infant's health condition is outputted depending upon a temperature of stool, sensed by the temperature sensor, whereby the infant's health can be easily checked whenever the infant empties the bowels, and an operating method thereof.

BACKGROUND ART

Generally, an infant has difficulties in properly showing feelings such as desire, discontent, pain, etc. In babyhood, if discontent or pain of an infant is not quickly cured, not only physical illness can be caused, but also mental health of the infant can be adversely affected. Accordingly, in order to ensure healthful growth of an infant, it is necessary to pay close attention to the infant. Specifically, it is important before everything else to find and cure a symptom at an early stage by periodically checking health of the infant.

However, it is impossible for a parent to take an infant to a hospital every day to check health of the infant. Also, it is difficult and cumbersome for a parent to check health of the infant every day at home.

DISCLOSURE OF THE INVENTION

Accordingly, the present invention has been made in consideration of the fact that a temperature of the human body, which is closely related with health of an infant, is most precisely measured at a region of the pancreas, and a temperature of stool which passed through the region of the pancreas, nearly approaches to a temperature of the region of the pancreas. Therefore, an object of the present invention is to provide an infant's chamber pot having a health checking function, in which a temperature sensor is disposed in a manner such that a character signal and/or a sound signal for notifying the infant's health condition is outputted depending upon a temperature of stool, sensed by the temperature sensor, whereby the infant's health can be easily and precisely checked whenever the infant empties the bowels, and an operating method thereof.

In order to achieve the above object, according to one aspect of the present invention, there is provided an infant's chamber pot comprising: a power source section; a temperature sensor installed on a bottom surface inside the chamber pot to measure a temperature of stool; a controller electrically connected to the temperature sensor, operated by a voltage supplied from the power source section and having a memory part in which melody signal data and warning signal data are stored, the controller selectively outputting the melody signal data or the warning signal data depending upon the stool temperature sensed by the temperature sensor, by comparing the stool temperature with a normal threshold temperature; and a speaker electrically connected to an output terminal of the controller, the speaker converting the signal data outputted from the controller into an audible signal and then, outputting the audible signal.

According to another aspect of the present invention, a display section for displaying a temperature which is obtained by correcting the stool temperature by virtue of the controller, is installed on an outer surface of the chamber pot and electrically connected to the controller.

According to still another aspect of the present invention, an operating switch is electrically connected between and to the controller and the power source section.

BRIEF DESCRIPTION OF THE DRAWINGS

The above objects, and other features and advantages of the present invention will become more apparent after a reading of the following detailed description when taken in conjunction with the drawings, in which.

BEST MODE FOR CARRYING OUT THE INVENTION

Figure 1:
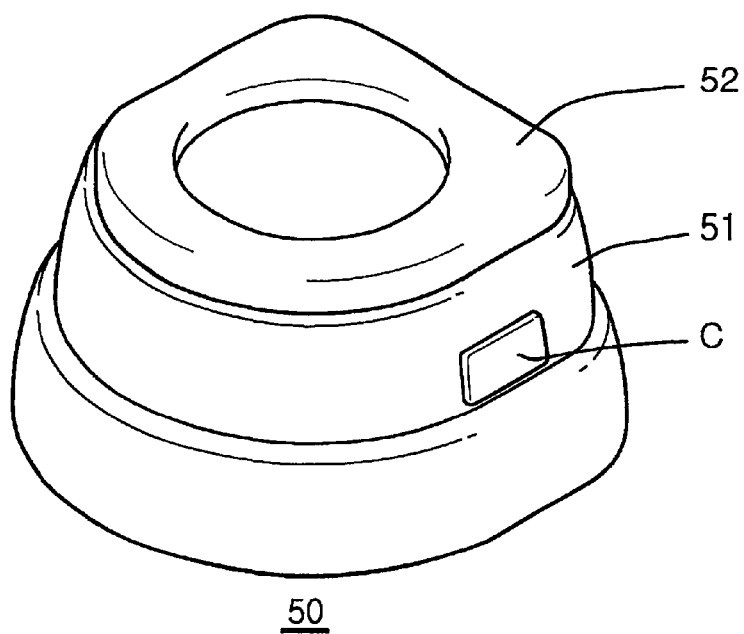
FIG. 1 is a perspective view illustrating an infant's chamber pot having a health checking function in accordance with an embodiment of the present invention.

Reference will now be made in greater detail to a preferred embodiment of the invention, an example of which is illustrated in the accompanying drawings. Wherever possible, the same reference numerals will be used throughout the drawings and the description to refer to the same or like parts.

Figure 2:
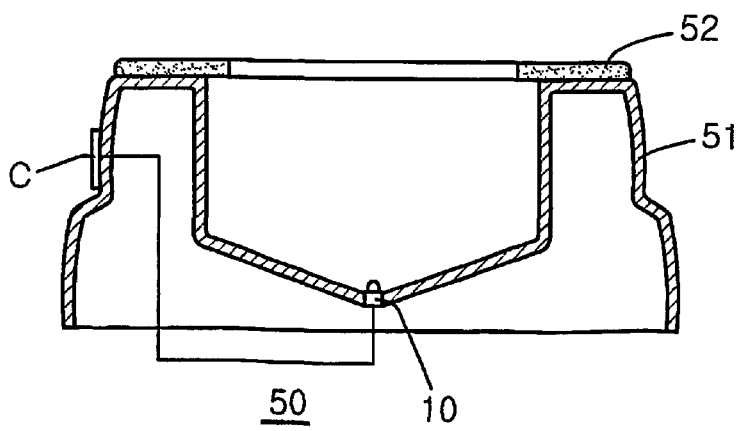
FIG. 2 is a side cross-sectional view of FIG. 1.
Figure 3:
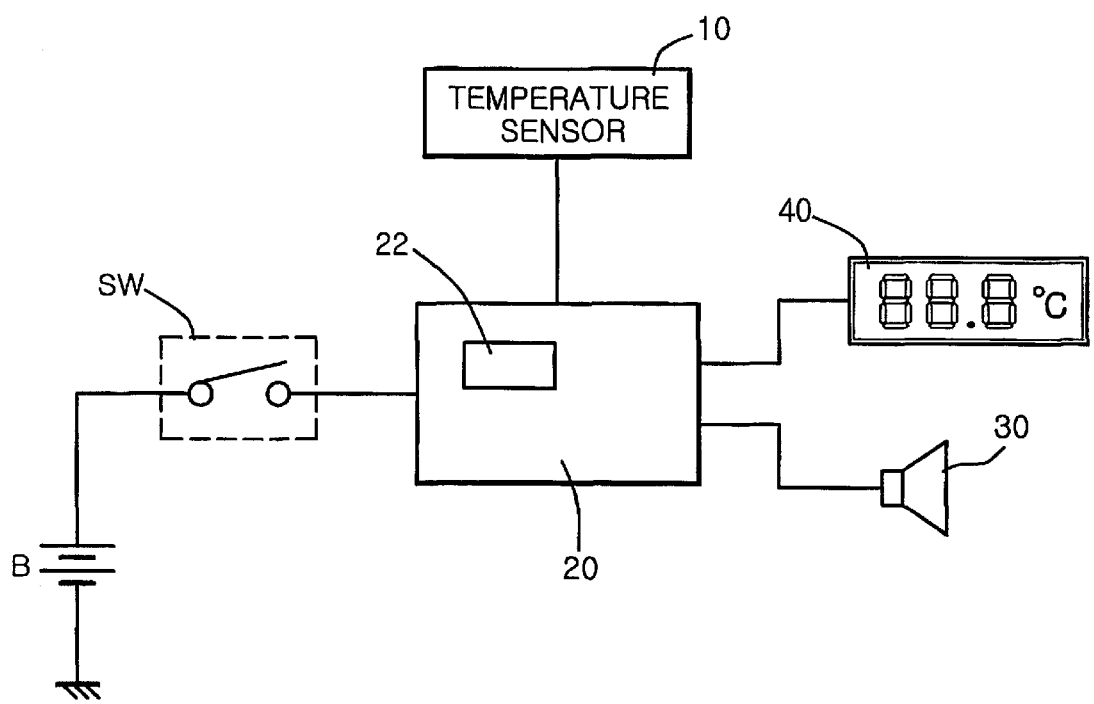
FIG. 3 is a circuit diagram of the infant's chamber pot having a health checking function according to the present invention.

FIG. 1 is a perspective view illustrating an infant's chamber pot having a health checking function in accordance with an embodiment of the present invention; FIG. 2 is a side cross-sectional view of FIG. 1; and FIG. 3 is a circuit diagram of the infant's chamber pot having a health checking function according to the present invention. As shown in FIGS. 1 through 3, an infant's chamber pot 50 according to the present invention includes a power source section B, a temperature sensor 10, a controller 20 and a speaker 30.

The temperature sensor 10 serves to sense a temperature of stool which is piled up in the chamber pot 50 as the infant empties the bowels. The temperature sensor 10 is fixedly installed on a bottom surface inside the chamber pot 50. Of course, the temperature sensor 10 should be installed on a lowermost portion inside the chamber pot 50 so that the temperature sensor 10 is covered by the stool piled up in the chamber pot 50 to precisely sense the stool temperature.

The controller 20 has a memory part 22 in which melody signal data and warning signal data are stored. The controller 20 is operated by a voltage which is supplied from the power source section B. The controller 20 is electrically connected to the temperature sensor 10. The controller 20 is configured in a manner such that it is selectively outputs the melody signal data or the warning signal data depending upon the stool temperature sensed by the temperature sensor 10, by comparing the stool temperature with a normal threshold temperature. At this time, among temperatures sensed by the temperature sensor 10, a maximum temperature value is stored in the controller 20, and the controller 20 selectively outputs the melody signal data or the warning signal data depending upon the maximum temperature valve.

The normal threshold temperature means a possible highest temperature value of stool which is evacuated by the infant having a normal body temperature. Due to the fact that the stool is evacuated through a region of the pancreas where a body temperature of the infant is measured, the normal threshold temperature can be set to 37° C. which corresponds to a body temperature of the infant having a normal health condition.

When the normal threshold temperature is set to 37° C., if the stool temperature sensed by the temperature sensor 10 is no greater than 37° C., the controller 20 outputs the melody signal data. On the contrary, if the stool temperature sensed by the temperature sensor 10 is no less than 37° C., the controller 20 outputs the warning signal data. As a consequence, a parent can readily recognize on the basis of the signal outputted from the controller 20, whether or not the infant has a normal health condition.

Further, in consideration of the fact that the stool temperature is slightly decreased depending upon an ambient temperature measured inside of the chamber pot 50, the controller 20 can be configured in a manner such that it can correct the stool temperature sensed by the temperature sensor 10.

That is to say, the ambient temperature dominating the inside of the chamber pot 50, which is sensed by the temperature sensor 10, is continuously stored in the controller 20. In this state, if the stool temperature is sensed by the temperature sensor 10 as the infant empties the bowels, the stool temperature is corrected in response to a most recently stored ambient temperature, and then, the corrected stool temperature is compared with the normal threshold temperature. In this way, health of the infant can be effectively checked. By performing experiments based on the fact that most chamber pots are used indoors, it was found that it is preferable to add 1.5° C. to the stool temperature which is sensed by the temperature sensor 10 and inputted into the controller 20 when the ambient temperature is 18–20° C. and 1.4° C to the stool temperature when the ambient temperature is 21–23° C.

The speaker 30 is electrically connected to an output terminal of the controller 20, and receives the melody signal data or the warning signal data which are outputted from the controller 20. The speaker 30 converts the signal data into an audible signal and outputs the audible signal. FIG. 2 illustrates a state wherein the power source section B, the controller 20 and the speaker 30 are assembled to define a module C. The module C is attached to a side surface of the chamber pot 50. The drawing reference numeral 52 represents a seating plate which is coupled to an upper surface of the chamber pot 50 and is made of a suitable material such as rubber or the like.

By the above-described construction, if the infant seats on the chamber pot 50 according to the present invention and evacuates the stool, the evacuated stool is piled up on the temperature sensor 10 which is installed on the bottom surface inside the chamber pot 50. Thereafter, a temperature of the stool is sensed by the temperature sensor 10 and is inputted into the controller 20. At this time, if the infant has a normal body temperature, the stool temperature which is sensed by the temperature sensor 10, is no greater than the normal threshold temperature, that is, 370° C., and according to this, the melody signal data are outputted from the controller 20. Thereupon, as a melody of a clear tone and rhythm is outputted from the speaker 30 which is connected to the output terminal of the controller 20, the parent readily recognizes that the infant has a normal body temperature.

On the contrary, if a body temperature of the infant is higher than a normal body temperature, the stool temperature which is sensed by the temperature sensor 10, is greater than the normal threshold temperature, that is, 37° C., and according to this, the warning signal data are outputted from the controller 20. Thereupon, as a predetermined warning sound is outputted from the speaker 30 which is connected to the output terminal of the controller 20, the parent readily recognizes that a body temperature of the infant is higher than the normal body temperature, whereby the parent can let the infant to undergo treatment of a medical specialist.

If a body temperature of the infant rises up to 38° C., brain cells of the infant are likely to be damaged, and, since a dangerous situation may result in, it is important to quickly take the infant to a medical specialist so that the infant can undergo proper treatment. In this regard, the controller 20 can be configured in a manner such that, with the normal threshold temperature (for example, 37° C.) and a critical threshold temperature (for example, 38°) set, the controller 20 can selectively output the melody signal data, first warning signal data or second warning signal data, depending upon the stool temperature which is sensed by the temperature sensor 10. The melody signal data are composed of clear music data which imply that the sensed stool temperature is no greater than the normal threshold temperature of 37° C. and thus the infant has a normal health condition. The first warning signal data are composed of light warning sound data which imply that the sensed stool temperature is between the normal threshold temperature of 37° C. and the critical threshold temperature of 38° C. and thus the infant has a slight fever. The second warning signal data are composed of strong warning sound data which imply that the sensed stool temperature is no less than 38° C. and thus the infant has a high fever. In this connection, it is to be readily understood that the melody signal data, the first warning signal data and the second warning signal data must be stored in advance in the memory part 22 of the controller 20.

Moreover, the signal data which are stored in the memory part 22, may be composed of sound messages such as 'normal', 'slight fever', 'high fever, let infant to undergo treatment of medical specialist' or the like.

While, in the above descriptions, the normal threshold temperature and the critical threshold temperature are set to 37° C. and 38° C., respectively, a person skilled in the art will readily understand that the threshold temperatures can be increased or decreased to some degree depending upon a physical constitution of the infant or a shape of the chamber pot, and an adjusting switch can be installed on the side surface of the chamber pot 50 to enable the parent directly adjust the threshold temperatures.

Further, a display section 40 for displaying a temperature which is sensed by the temperature sensor 10, can be coupled to an outer surface of the chamber pot 50 in such a way as to be connected with the controller 20. By this construction, because the parent can concretely recognize a stool temperature of the infant through the display section 40, it is possible to precisely check a change in body temperature of the infant on the basis of stool temperatures sensed whenever the infant empties the bowels. Also, the controller 20 can be configured in a manner such that it displays on the display section 40 letters such as 'normal', 'slight fever', 'high fever', etc. depending upon a temperature which is sensed by the temperature sensor 10. Furthermore, it can be envisaged that indicator lamps having colors such as red, green, and so forth, are lighted or flickered.

Also, by electrically connecting an operating switch SW between and to the controller 20 and the power source section B, only when the operating switch SW is turned on, the controller 20 can be appropriately operated, whereby unnecessary power consumption can be minimized. The operating switch SW can comprise a push button which is installed on the side surface of the chamber pot 50, a contact sensor which is installed between a body 51 and the seating plate 52 of the chamber pot 50 in a manner such that the contact sensor can be switched on when the infant seats on chamber pot 50, or the like.

Figure 4:
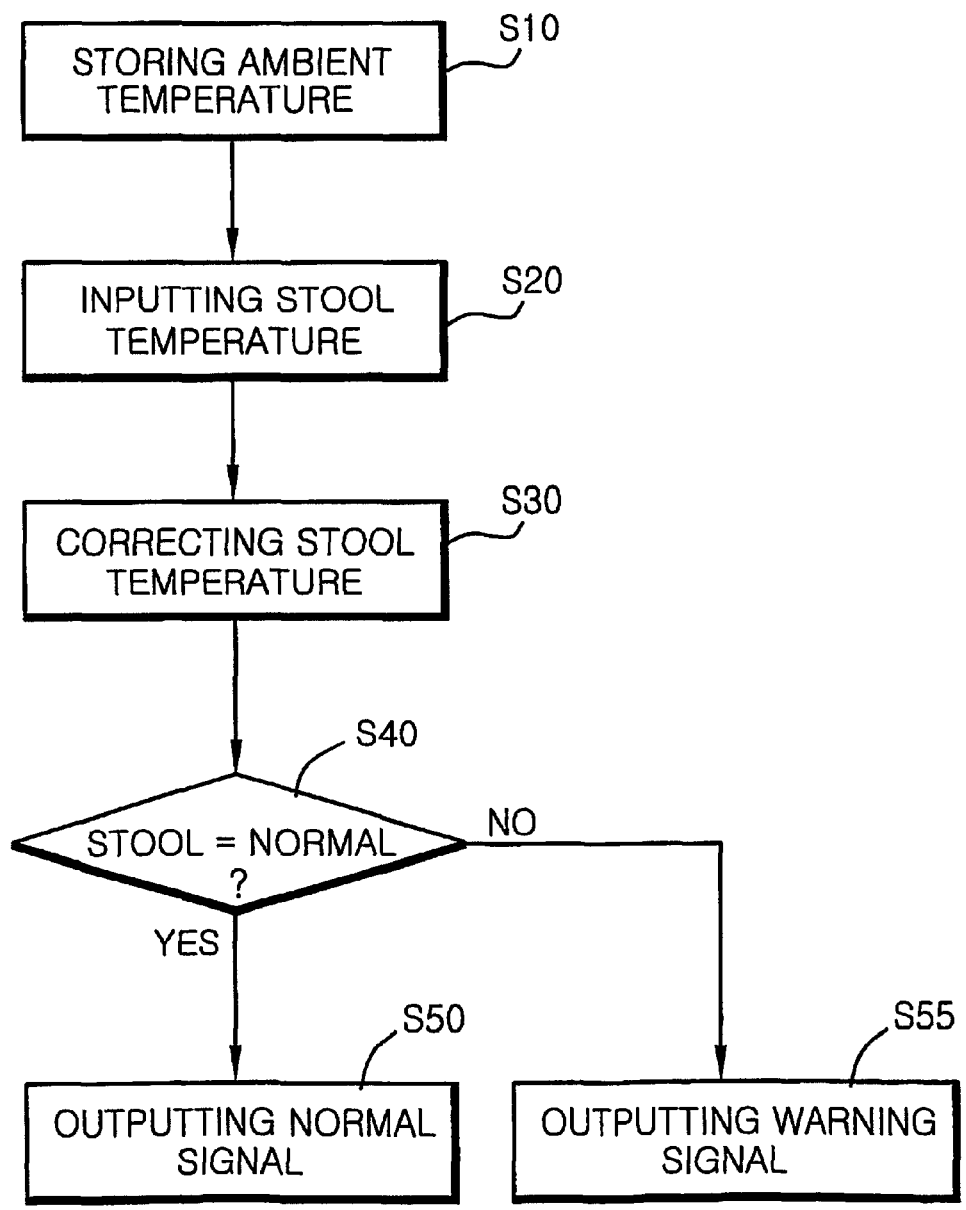
FIG. 4 is a flow chart for explaining an operating method of the infant's chamber pot having a health checking function according to the present invention.

FIG. 4 is a flow chart for explaining an operating method of the infant's chamber pot having a health checking function according to the present invention. As can be readily seen from FIG. 4, a method for operating an infant's chamber pot according to the present invention includes an ambient temperature storing step S10, a stool temperature receiving step S20, a stool temperature correcting step S30, a stool temperature comparing step S40, a normal signal outputting step S50 and a warning signal outputting step S55.

First, if the chamber pot 50 according to the present invention starts to operate, the ambient temperature storing step S10 of storing an ambient temperature dominating the inside of the chamber pot 50, which is sensed by the temperature sensor 10, is implemented. While implementing the ambient temperature storing step S10, if the infant evacuates stool, a stool temperature receiving step S20 of receiving a stool temperature which is sensed by the temperature sensor 10, is implemented. Generally, since it is the norm that an ambient temperature is no greater than 30° C. and a stool temperature of the infant is no less than 30° C., it is preferred that, when a temperature sensed by the temperature sensor 10 exceeds 30° C., the controller 20 determines the temperature as the stool temperature of the infant.

In the stool temperature correcting step S30 which is implemented after the stool temperature receiving step S20, in response to a most recently stored ambient temperature which is stored in the controller 20 in the ambient temperature storing step S10, the stool temperature which is inputted into the controller 20 in the stool temperature receiving step S20, is properly corrected. At this time, if the most recently stored ambient temperature is 18–20° C., a correcting value of 1.5° C. is added to the received stool temperature, and if the most recently stored ambient temperature is 21–23° C., it is sufficient that a correcting value of 1.4° C. is added to the received stool temperature. A correcting value can be slightly varied depending upon a size and a material of the chamber pot and an ambient temperature.

After the stool temperature correcting step S30 is implemented, the stool temperature comparing step S40 of comparing the corrected stool temperature with the normal threshold temperature is implemented in such a way as to determine whether or not the stool temperature is within a normal temperature range.

If it is determined in the stool temperature comparing step S40 that the corrected stool temperature is no greater than the normal threshold temperature, the normal signal outputting step S50 of judging the corrected stool temperature to be normal, and then outputting a normal signal, that is, a melody signal, lighting a green lamp or displaying 'normal', which indicates a normal health condition, is implemented.

Also, If it is determined in the stool temperature comparing step S40 that the corrected stool temperature is greater than the normal threshold temperature, the warning signal outputting step S55 of judging the corrected stool temperature to be abnormal, and then outputting a warning signal, that is, a warning signal, lighting a red lamp or displaying 'abnormal', which indicates an abnormal health condition, is implemented, whereby a parent can recognize at an early stage that health of the infant is impaired.

INDUSTRIAL APPLICABILITY

As a result, an infant's chamber pot having a health checking function and an operating method thereof according to the present invention provide advantages in that, since a body temperature of an infant is sensed using a temperature of stool whenever the infant empties the bowels, and a character signal or a sound signal is outputted in such a way as to notify a parent of the infant's health condition, a parent can check every day a change in the body temperature of the infant and thereby health of the infant. Consequently, if the body temperature of the infant rises by the presence of a disease, the parent can find the disease at an early stage and let the infant to undergo treatment of a medical specialist, whereby healthful growth of the infant is ensured.

In the drawings and specification, there have been disclosed typical preferred embodiments of the invention and, although specific terms are employed, they are used in a generic and descriptive sense only and not for purposes of limitation, the scope of the invention being set forth in the following claims.

What is claimed is:

1. An infant's chamber pot comprising:

a power source section;

a temperature sensor installed on a bottom surface inside the chamber pot to measure a temperature of stool;

a controller electrically connected to the temperature sensor, operated by a voltage supplied from the power source section and having a memory part in which melody signal data and warning signal data are stored, the controller selectively outputting the melody signal data or the warning signal data depending upon the stool temperature sensed by the temperature sensor, by comparing the stool temperature with a normal threshold temperature; and a speaker electrically connected to an output terminal of the controller, the speaker converting the signal data outputted from the controller into an audible signal and then, outputting the audible signal.

2. The infant's chamber pot as claimed in claim 1, wherein the controller is configured in a manner such that the controller stores an ambient temperature sensed by the temperature sensor inside the chamber pot, and, when the stool temperature is sensed by the temperature sensor, the controller corrects the stool temperature in response to a most recently stored ambient temperature.

3. The infant's chamber pot as claimed in claim 2, wherein a display section for displaying a temperature which is obtained by correcting the stool temperature by virtue of the controller, is installed on an outer surface of the chamber pot and electrically connected to the controller.

4. The infant's chamber pot as claimed in claim 2, wherein the warning signal data which are stored in the memory part of the controller, are divided into first warning signal data and second warning signal data, and wherein the controller is configured in a manner such that the controller selectively outputs the melody signal data, the first warning signal data or the second warning signal data depending upon the stool temperature sensed by the temperature sensor, by comparing the stool temperature with the normal threshold temperature and a critical threshold temperature.

5. The infant's chamber pot as claimed in claim 1, wherein an operating switch is electrically connected between and to the controller and the power source section.

6. The infant's chamber pot as claimed in claim 5, wherein the operating switch comprises a contact sensor which is installed on an upper surface of the chamber pot so that the contact sensor is turned on when the infant sits on the chamber pot.

7. The infant's chamber pot as claimed in claim 1, wherein a display section for displaying a temperature which is obtained by correcting the stool temperature by virtue of the controller, is installed on an outer surface of the chamber pot and electrically connected to the controller.

8. The infant's chamber pot as claimed in claim 1, wherein the warning signal data which are stored in the memory part of the controller, are divided into first warning signal data and second warning signal data, and wherein the controller is configured in a manner such that the controller selectively outputs the melody signal data, the first warning signal data or the second warning signal data depending upon the stool temperature sensed by the temperature sensor, by comparing the stool temperature with the normal threshold temperature and a critical threshold temperature.

9. A method for operating an infant's chamber pot having a health checking function, comprising:

an ambient temperature storing step of storing an ambient temperature sensed by a temperature sensor;

a stool temperature receiving step of receiving a stool temperature sensed by the temperature sensor;

a stool temperature correcting step of correcting the stool temperature received in the stool temperature receiving step, depending upon a most recently stored ambient temperature stored in the ambient temperature storing step;

a stool temperature comparing step of comparing the stool temperature corrected in the stool temperature correcting step, with a normal threshold temperature;

a normal signal outputting step of judging the corrected stool temperature to be normal when it is determined in the stool temperature comparing step that the corrected stool temperature is no greater than the normal threshold temperature, and then outputting a normal signal which indicates a normal health condition; and a warning signal outputting step of judging the corrected stool temperature to be abnormal when it is determined in the stool temperature comparing step that the corrected stool temperature is greater than the normal threshold temperature, and then outputting a warning signal which indicates an abnormal health condition.

* * * * *

UNITED STATES PATENT AND TRADEMARK OFFICE
CERTIFICATE OF CORRECTION

PATENT NO. : 6,684,418 B2 Page 1 of 1
DATED : February 3, 2004
INVENTOR(S) : Keon S. Choi It is certified that error appears in the above-identified patent and that said Letters Patent is hereby corrected as shown below:

Title page,
Insert Item:
-- [30]  Foreign Application Priority Data
    Korea    2000-14420    05/22/2000 --.
Item [22], PCT Filed, please delete "11/25/2002" and substitute -- 11/22/02 --.

Signed and Sealed this

Thirty-first Day of May, 2005

JON W. DUDAS
*Director of the United States Patent and Trademark Office*